(12) United States Patent
Breitenmoser et al.

(10) Patent No.: US 11,457,320 B2
(45) Date of Patent: Sep. 27, 2022

(54) SELECTIVELY COLLECTING AND STORING SENSOR DATA OF A HEARING SYSTEM

(71) Applicant: Sonova AG, Staefa (CH)

(72) Inventors: Andreas Breitenmoser, Zurich (CH); Peter Derleth, Hinwil (CH); Harald Krueger, Affoltern (CH); Aliaksei Tsitovich, Stäfa (CH)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 17/207,870

(22) Filed: Mar. 22, 2021

(65) Prior Publication Data

US 2021/0306774 A1 Sep. 30, 2021

(30) Foreign Application Priority Data

Mar. 25, 2020 (EP) .................................... 20165616

(51) Int. Cl.
*H04R 25/00* (2006.01)

(52) U.S. Cl.
CPC ..... *H04R 25/554* (2013.01); *H04R 2225/025* (2013.01); *H04R 2225/41* (2013.01); *H04R 2225/55* (2013.01)

(58) Field of Classification Search
CPC .......... H04R 2225/025; H04R 2225/41; H04R 2225/55; H04R 25/554; H04R 25/30; H04R 25/50
USPC ....................................................... 381/315
See application file for complete search history.

(56) References Cited

U.S. PATENT DOCUMENTS

| 7,242,777 | B2 | 7/2007 | Leenen et al. |
| 7,783,066 | B2 | 8/2010 | Naylor |
| 7,974,716 | B2 | 7/2011 | Schumaier |
| 8,406,440 | B2 | 3/2013 | Kidmose |
| 8,582,790 | B2 | 11/2013 | Knox et al. |
| 8,588,442 | B2 | 11/2013 | Schmitt et al. |
| 8,917,833 | B1 | 12/2014 | Henderson |
| 9,301,057 | B2 | 3/2016 | Sprague et al. |

(Continued)

FOREIGN PATENT DOCUMENTS

| EP | 2063663 A1 | 5/2009 |
| EP | 2884766 | 6/2015 |
| WO | 2017211426 A1 | 12/2017 |

OTHER PUBLICATIONS

European Patent Office, European Search Report for EP20165616.2, dated May 8, 2020, Rijswijk, Netherlands.

(Continued)

*Primary Examiner* — Phylesha Dabney
(74) *Attorney, Agent, or Firm* — ALG Intellectual Property, LLC (57) ABSTRACT

A method for collecting and storing sensor data (56, 64) of a hearing system (10) comprises: receiving the sensor data (56, 64) of at least one sensor (20, 32, 34) of a hearing device (12) of the hearing system (10), wherein the hearing device (12) is worn by a user; detecting a situation (72) of interest by classifying at least a part of the sensor data (56, 64) with a classifier (61) implemented in the hearing system (10); collecting the sensor data (56, 64), when the hearing system (10) is in a situation (72) of interest; and sending the collected sensor data (76) to a storage system (54) in data communication with the hearing system (10).

16 Claims, 2 Drawing Sheets

(56) References Cited

U.S. PATENT DOCUMENTS

| | | |
|---|---|---|
| 10,237,664 B2 | 3/2019 | Smith et al. |
| 2011/0293123 A1 | 12/2011 | Neumeyer et al. |
| 2015/0355880 A1 | 12/2015 | Kraft et al. |
| 2016/0142820 A1 | 5/2016 | Kraft et al. |
| 2017/0127201 A1 | 5/2017 | Roeck et al. |
| 2019/0020959 A1 | 1/2019 | Ungstrup et al. |
| 2019/0052978 A1* | 2/2019 | Hannemann ......... H04R 25/505 |
| 2019/0122125 A1 | 4/2019 | Dragicevic et al. |
| 2019/0231253 A1 | 8/2019 | Ahmed et al. |

OTHER PUBLICATIONS

"Communication pursuant to Article 94(3) EPC", received in E.P. Patent Application No. 20165616.2, dated Jul. 13, 2021.

"Summons to attend oral proceedings pursuant to Rule 115(1) EPC", received in E.P. Patent Application No. 20165616.2, Dated Feb. 21, 2022.

* cited by examiner

SELECTIVELY COLLECTING AND STORING SENSOR DATA OF A HEARING SYSTEM

TECHNICAL FIELD

The present technology relates to a method, a computer program and a computer-readable medium for collecting and storing sensor data of a hearing system. Furthermore, the present technology relates to a hearing system with a hearing device and optionally a mobile device.

BACKGROUND

Hearing devices are generally small and complex devices. Hearing devices can include a processor, microphone, speaker, memory, housing, and other electronical and mechanical components. Some example hearing devices are Behind-The-Ear (BTE), Receiver-In-Canal (RIC), In-The-Ear (ITE), Completely-In-Canal (CIC), and Invisible-In-The-Canal (IIC) devices. A user can prefer one of these hearing devices compared to another device based on hearing loss, aesthetic preferences, lifestyle needs, and budget.

Together with a mobile device, which is in data communication with the hearing device, the hearing device may form a hearing system, which may support a user by compensating his or her hearing loss. A hearing system incorporates many parts, such as hardware, software, algorithms, fitting formulas, etc., which need to be designed, configured, adjusted and/or tuned based on data. Such data may include audio data, activity data and health data. All this data may be indicative of the needs of the user.

Datasets of these data may be acquired from third parties, for example other companies and universities, created by simulation or in an experimental setup, and may be collected in the field. However, to acquire valuable data may be cumbersome. Meaningful datasets may be expensive to purchase, difficult to simulate or laborious to collect.

SUMMARY

It is an objective of the present disclosure to simplify the fitting, configuration and training of hearing devices and in particular hearing device algorithms and models, for example by providing good configuration values. A further objective of the present disclosure is to improve the quality of the training data for these tasks.

These objectives are achieved by the subject-matter of the independent claims. Further exemplary embodiments are evident from the dependent claims and the following description.

A first aspect of the present technology relates to a method for collecting and storing sensor data of a hearing system. The hearing system may comprise a hearing device and optionally a mobile device. The hearing device may be worn by a user, for example behind the ear or in the ear. The hearing device may be a hearing aid for compensating a hearing loss of a user. Here and in the following, when to a hearing device is referred, also a pair of hearing devices, i.e. a hearing device for each ear of the user, may be meant. A hearing device may comprise one or two hearing aids and/or a cochlear implant.

According to an embodiment, the method comprises: receiving the sensor data of at least one sensor of a hearing device of the hearing system, wherein the hearing device is worn by a user. The at least one sensor may comprise a microphone, a motion sensor, an acceleration sensor, a position sensor, a medical sensor, etc. The sensor data may be acquired with sensors of the hearing device and optionally the mobile device. Also the receiver/transmitters for wireless data communication of the hearing device and/or the mobile device may be seen as sensors.

According to an embodiment, the method further comprises: detecting a situation of interest by classifying at least a part of the sensor data with a classifier implemented in the hearing system. The classifier may be a program module run in the hearing device and/or the mobile device, which is adapted to discriminate between situations of interest and situations of disinterest. Here, the term "interest" refers to situations, where data collection may be of interest. Situations of interest and situations of disinterest may be simply coded with "1" and "0", which may be a possible output of the classifier. Alternative terms for the classifier may be detector, selector, filter, identifier" and/or predictor. In general, the classifier may detect and/discriminate between valuable and less valuable situations.

A classification does not need to be binary, for example discriminating between classes "1" and "0". There may be multiple classes, for example, where one is not interesting, one is less interesting, one is more interesting, and one is fully interesting. Each of these classes may relate to a different data gathering, such as varying frequency and/or duration of data gathering.

In general, a situation of interest may be represented by a specific set of configuration parameters of the classifier. These configuration parameters may comprise ranges and/or thresholds for classification values generated by the classifier, rules used by the classifier, weights used by the classifier, etc.

The input of the classifier may be a part of the sensor data, such as audio data, motion data, acceleration data, position data, medical data, etc. The classifier may have several subcomponents, which, for example, classify the sensor data of different sensors into several classification values, which are then further processed by a further subcomponent, which decides, whether a situation of interest is present. The further subcomponent may be based on rules and/or comparators with threshold values.

Examples for a classifier or in particular for a subcomponent may be machine learning algorithms like a probabilistic classifier, such as logistic regression, an artificial neural network trained for classification, or a large margin classifier, such as a support vector machine (SVM), which may separate the sensor data or classification values determined therefrom into several classes. The SVM, for example, may separate the classes by a set of hyperplanes, each of which maximizes the margin, respectively distance, between the data points of two different classes.

Further inputs to the classifier may be user input and/or performance measures of the hearing system. For example, a sound classifier may report that audio sensor data cannot be allocated to a pre-set sound class with a sufficient reliability/confidence. Such a situation, i.e. non-allocatable audio data, also may be classified as a situation of interest.

The reliability/confidence may be described by measures, such as confidence scores or probabilities, which can also be seen as classification values. For example, the confidence scores of an SVM may be calculated as the distance of a data point from separating hyperplanes (i.e. the smaller the distance the less confident). The reliability/confidence may also be expressed as the probability of a data point belonging to a certain class, for example resulting from Platt scaling in the case of the SVM (i.e. running a logistic regression on the SVM's confidence scores). Alternatively, the accuracy of a probabilistic prediction can be measured by the mean square difference between the predicted probability and the actual classification outcome, using the Brier score loss for example.

The classifier may be seen as a detector and/or filter, which detects and/or filters for interesting and/or valuable situations. Such situations may provide valuable data for the creation of a dataset, which may be further used for fitting, training, configuring, etc. of hearing devices.

In general, a situation of interest may be representative for a certain use case, such as speech in loud noise, binaural beamforming, etc.

According to an embodiment, the method further comprises: collecting the sensor data, when the hearing system is in a situation of interest and sending the collected sensor data to a storage system in data communication with the hearing system. When a situation of interest is detected, the received sensor data is collected. This may mean that the sensor data is buffered in a memory of the hearing system. Otherwise, i.e. when the hearing system is not in a situation of interest, the received sensor data may be discarded, i.e. not buffered in the memory of the hearing system.

In other words, the hearing system may solely collect sensor data, when the classifier has detected a situation of interest. In such a way, resources of the hearing system may be saved.

Collected and/or buffered sensor data may be sent to a storage system that may be provided by a hearing device manufacturer. The storage system may be part of an Internet server and/or a cloud server, which is in data communication with the hearing system. The collected and/or buffered sensor data then may be stored in the storage system, in particular with respect to the detected situation of interest. The storage system may store the collected sensor data of a plurality of hearing systems. In such a way, for every situation of interest, large amounts of training data and/or testing data may be collected.

For example, the collected sensor data may be fed into existing datasets for training or testing purposes. The collected sensor data may be used for continuous learning and/or improvements of configurations, parameters, algorithms, methods, models, etc. of concern to the hearing system. The collected sensor data may be supplemented with data from other sources, such as manually recorded and labelled and/or purchased data. This may lead to even more diverse and/or balanced datasets.

According to an embodiment, the classifier comprises a sound classifier for classifying audio data, which is received by the hearing device and which is output by the hearing device to the user. The sound classifier may be a subcomponent of the classifier. For example, the sound classifier may output a volume, frequencies, a sound direction as classification values. It also may be that the sound classifier outputs properties of the audio signal, such as speech in noise, music, wind noise, etc., as classification values.

It may be that audio data from the microphone of hearing device and/or streamed audio data from the mobile device, for example during a telephone call, are processed by the sound classifier.

According to an embodiment, classification values of the sound classifier are used for selecting hearing programs of the hearing device. In specific hearing devices, such a sound classifier already may be present. A hearing program may be a software module of the hearing device adapted for processing audio data in a specific way before the audio data is provided to the user. For example, a hearing program may suppress noise, may frequency dependent attenuate the audio data, may compress and/or shift frequency ranges, etc.

According to an embodiment, the sensor data comprises at least one of motion data acquired with a motion sensor, position data acquired with a position sensor and medical data acquired with a medical data sensor. Further sensor data from further sensors may be used for classification and also may be collected, when a situation of interest is detected.

The motion sensor may be an acceleration sensor and/or may be a part of the hearing device and/or the mobile device. With the motion data of the hearing device, head movements of the user may be determined.

The position sensor may be a part of the hearing device and/or the mobile device, for example a GPS sensor. With the position data, a location of the user, such as his home, his office, a restaurant, etc. may be discriminated.

The medical data sensor may be a part of the hearing device and/or the mobile device. The medical data may include information on pulse, heart frequency, breathing frequency of the user. The medical data sensor, in particular of the hearing device, may be a photoplethysmography (PPG) sensor.

In general, the sensor data may include audio data (comprising speech, noise, and music) originating from listening situations, activity data (such as accelerometer readings), originating from movement patterns or user interaction situations and/or medical data (such as PPG readings), originating from daily routines or stress situations.

According to an embodiment, the classifier comprises an additional data classifier into which at least one of the motion data, acceleration data, position data and medical data are input. The additional data classifier may be based on a machine learning algorithm, which evaluates these types of data. The additional data classifier may identify supplemental information adapted for discriminating situations of interest, such as head movements, locations, emotional conditions of the user, such as stress, etc.

According to an embodiment, user input into the hearing system is input into the classifier. The user input may be the selection of a specific hearing program and/or may be a selection of a specific situation of interest. A set of possible hearing programs and/or situations of interest may be provided to the user with a user interface of the hearing system. With this user interface, the user may select hearing programs and/or situations of interest.

The user may help to detect situations of interest for data gathering by providing user input, such as pushing a button on a graphical user interface on the mobile device in order to acknowledge that a data of a listening situation shall be recorded. Also, the user may provide ground truth and/or labels for the data recorded. The user may attribute, confirm, and/or enter data labels as well as properties of the specific situation of interest via the graphical user interface or an interface on the hearing device.

According to an embodiment, classification values generated by the classifier are compared with threshold values for detecting a situation of interest. One way of detecting situations of interest is by determining, whether a set of quantities, which may be output by subcomponents of the classifier, is within or without specific bounds. These bounds and/or threshold values may be seen as configuration parameters of the classifier and/or this subcomponent.

According to an embodiment, the method further comprises: detecting a situation of disinterest by classifying at least a part of the sensor data with the classifier. It also may be that the classifier determines, whether sensor data should not be collected. In this case, the sensor data is discarded, when the hearing system is in a situation of disinterest.

According to an embodiment, the sensor data is collected, when the hearing device is not in a situation of disinterest. In other words, the hearing system may be in a situation of interest, when it is not in a situation of disinterest. Such situations may result in sensor data that may be useful for being further evaluated.

According to an embodiment, the method further comprises: sending configuration parameters for the classifier for a specific situation of interest from the storage system to a plurality of hearing systems. The configuration parameters may comprise weights, settings, bounds and/or thresholds encoding a situation of interest for the classifier. In such a way, when further data is needed in the storage system, this data may be demanded by notifying the hearing systems accordingly.

According to an embodiment, the hearing system comprises a mobile device carried by the user. The mobile device may be a smartphone or a smartwatch. The mobile device may be in wireless data communication with the hearing device, for example via Bluetooth.

According to an embodiment, at least a part of the classifier is implemented in the mobile device. The sensor data may be sent from the hearing device to the mobile device and may be classified there. This may save computing resources of the hearing device.

It also may be that sensor data acquired by the mobile device is classified there, such it is not necessary to send it to the hearing device.

According to an embodiment, first sensor data from a first sensor is collected, wherein the classifier generates a classification of second sensor data from a second sensor. The first sensor data then may be labelled with the classification of the second sensor. For example, the mobile device may classify an audio stream acquired with its microphone with respect to environmental noise. This classification may be used for labelling the audio data acquired with the microphone of the hearing device.

In such a way, the first sensor data may be automatically labelled, which may be of importance for supervised learning. It also may be that labelling is performed based on other data, such as actual configuration parameters of the hearing device, for example, which hearing program is running. As a further option, the user also may perform the task of labelling or suggesting labels, for example via selecting labels on the user interface.

According to an embodiment, the storage system is connected via Internet with the hearing system. The storage system may be a part of a server system of a hearing device manufacturer, which uses the storage system for testing, training, configuration and fitting of hearing devices. The collected sensor data of a plurality of hearing devices may be sent to the storage system via Internet.

The collected sensor data may be transmitted to the storage system in selected time windows, when the hearing system is in a mode of reduced operation. For example, this may be done during the night, or when the hearing device is in a standby mode.

According to an embodiment, the storage system comprises a further classifier for classifying, whether the collected sensor data is sensor data of interest. It may be that the sensor data is classified for a second time at the site of the storage system. It may be that the storage system solely stores collected sensor data of interest, which has also been classified as being of interest by the storage system.

Further aspects of the present technology relate to a computer program for collecting and storing sensor data of a hearing system, which, when being executed by a processor, is adapted to carry out the steps of the method as described in the above and in the following as well as to a computer-readable medium, in which such a computer program is stored.

For example, the computer program may be executed in a processor of the hearing device, which hearing device, for example, may be carried by the person behind the ear. The computer-readable medium may be a memory of this hearing device. The computer program also may be executed by a processor of the mobile device and the computer-readable medium may be a memory of the mobile device. It also may be that steps of the method are performed by the hearing device and other steps of the method are performed by the mobile device.

In general, a computer-readable medium may be a floppy disk, a hard disk, an USB (Universal Serial Bus) storage device, a RAM (Random Access Memory), a ROM (Read Only Memory), an EPROM (Erasable Programmable Read Only Memory) or a FLASH memory. A computer-readable medium may also be a data communication network, e.g. the Internet, which allows downloading a program code. The computer-readable medium may be a non-transitory or transitory medium.

Further aspects of the present technology relate to the hearing device as described above and below and/or to a hearing system comprising such a hearing device. The hearing system optionally may comprise a mobile device as described above and below. The hearing device and/or the hearing system may be adapted for performing the method as described above and below.

It has to be understood that features of the method as described in the above and in the following may be features of the computer program, the computer-readable medium, the hearing device and the hearing system as described in the above and in the following, and vice versa.

These and other aspects of the present technology will be apparent from and elucidated with reference to the embodiments described hereinafter.

BRIEF DESCRIPTION OF THE DRAWINGS

Below, embodiments of the present technology are described in more detail with reference to the attached drawings.

The reference symbols used in the drawings, and their meanings, are listed in summary form in the list of reference symbols. In principle, identical parts are provided with the same reference symbols in the figures.

DETAILED DESCRIPTION OF EXEMPLARY EMBODIMENTS

Figure 1:
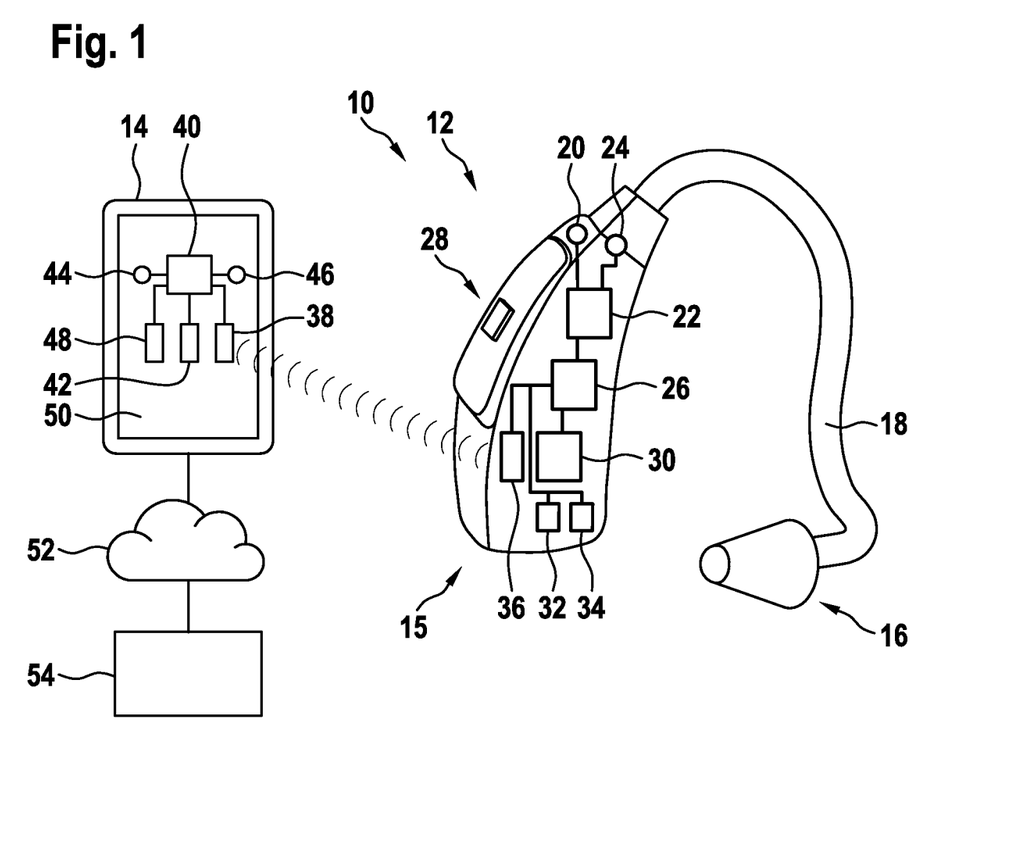
FIG. 1 schematically shows a hearing system according to an embodiment of the present technology.

FIG. 1 schematically shows a hearing system 10 with a hearing device 12 in the form of a behind-the-ear device and a mobile device 14. It has to be noted that the hearing device 12 is a specific embodiment and that the method described herein also may be performed by other types of hearing devices, such as in-the-ear devices.

The hearing device 12 comprises a part 15 behind the ear and a part 16 to be put in the ear channel of a user. The part 15 and the part 16 are connected by a tube 18. In the part 15, a microphone 20, a sound processor 22 and a sound output device 24, such as a loudspeaker, are provided. The microphone 20 may acquire environmental sound of the user and may generate a sound signal, the sound processor 22 may amplify the sound signal and the sound output device 24 may generate sound that is guided through the tube 18 and the in-the-ear part 16 into the ear channel of the user.

The hearing device 12 may comprise a processor 26, which is adapted for adjusting parameters of the sound processor 22, such that an output volume of the sound signal is adjusted based on an input volume. These parameters may be determined by a computer program run in the processor 26. For example, with a knob 28 of the hearing device 12, a user may select a modifier (such as bass, treble, noise suppression, dynamic volume, etc.) and levels and/or values of these modifiers may be selected, which influence the frequency dependent gain and the dynamic volume of the sound processor 22. All these functions may be implemented as computer programs stored in a memory 30 of the hearing device 12, which computer programs may be executed by the processor 22.

The hearing device 12 furthermore may comprise an acceleration sensor 32 and/or a medical sensor 34. With the acceleration sensor 32, a movement of the head of the user of the hearing device 12 may be determined. With the medical sensor 34, which may be a photoplethysmography (PPG) sensor, a heart pulse and/or further medical conditions of the user, such as a breathing speed, can be determined.

The hearing device 12 also may comprise a sender/receiver 36 for (for example wireless) data communication with a sender/receiver 38 of the mobile device 14, which may be a smartphone or tablet computer. As the hearing device 12, the mobile device 14 comprises a processor 40 and memory 42, in which programs are stored, which may be executed by the processor 40. The mobile device 14 may comprise a microphone 44, which may acquire environmental sound of the user. The mobile device may comprise a loudspeaker 46, which may be used for outputting sound, such as during a telephone call. Furthermore, the mobile device 14 may comprise a position sensor 48, such as a GPS sensor.

With a user interface 50, the user of the hearing system 10 may interact with programs of the hearing system 10, and for example may adjust modifiers of the hearing device 12, which influence the frequency dependent gain and the dynamic volume of the sound processor.

The mobile device 14 may be adapted for data communication via the Internet 52. For example, as described above and below, collected sensor data may be sent via the Internet to a storage system 54, where the collected sensor data can be used for configuration, training and fitting of further hearing devices.

Figure 2:
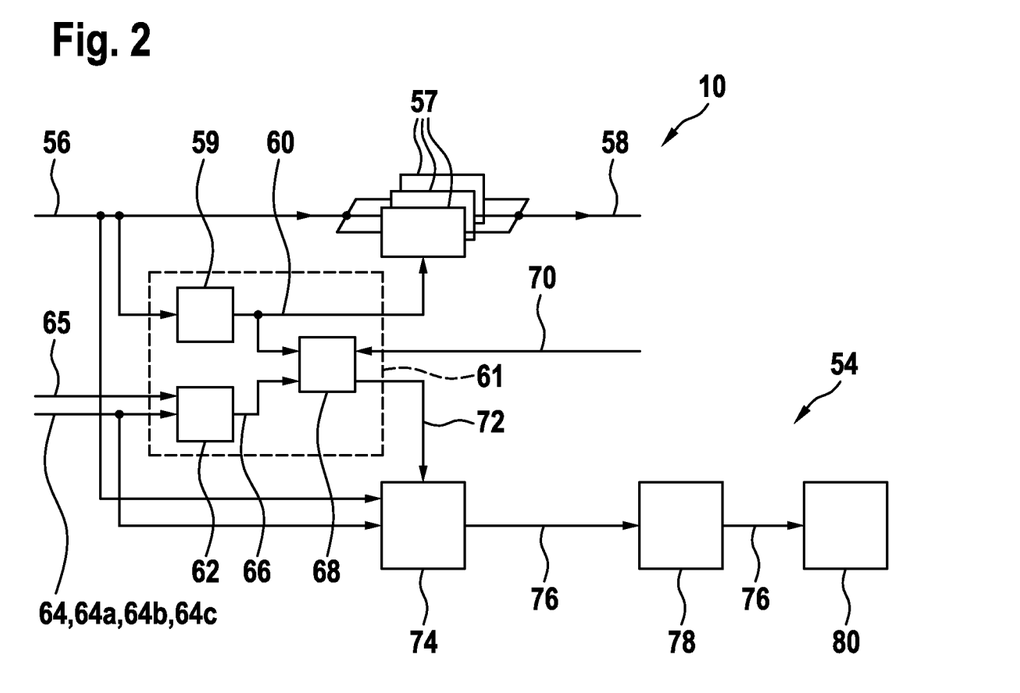
FIG. 2 schematically shows a functional diagram of a hearing system according to an embodiment of the present technology, which is also used for illustrating a method according to an embodiment of the present technology.

FIG. 2 shows a functional diagram of the hearing system 10 and the storage system 54. The blocks shown in FIG. 2 all may be computer program modules that may be run in the hearing device 12, the mobile device 14 and optionally the storage system 54.

FIG. 2 shows that audio data 56 is input into several hearing programs 57, which generate an output audio signal 58, which may be output to the user of the hearing system 10. The audio data 56 may be generated by the microphone 20 of the hearing device 12 and/or may be sent from the mobile device 14 to the hearing device 12. In this case, the audio data 56 may be generated by the microphone 44 of the mobile device 14 and/or may be received via Internet 52 and/or via a mobile telephone network during a telephone call.

The hearing programs 57, which may be run by the sound processor 22 and/or the processor 26 of the hearing device 12, process the audio data 56 to adapt it to the hearing needs of the user. For example, the sound programs 57 may attenuate specific frequency of the audio data 56, may compress and shift frequencies, etc.

Which hearing program 57 is selected and/or how processing parameters of the hearing programs are tuned are determined by a sound classifier 59. The sound classifier 59, which may be a program module of the hearing device 10, receives the audio data 56 and generates sound classification values 60, which for example, encode, whether the audio data 56 contains speech, noise, speech in noise, music, wind noises, etc. The sound classification values 60 are then used to select a suitable hearing program 57 and/or to tune it.

The sound classifier 59 may be part of a situation classifier 61, which, in general, is a classifier, which receives sensor data 56, 64 of at least one sensor 20, 32, 34 of the hearing device 12 and/or the mobile device 14. The situation classifier 61 may comprise the sound classifier 59 as subcomponent for classifying audio data 56, which is received by the hearing device 12 and which is output by the hearing device 12 to the user.

Beside the audio data 56, which may be seen as sensor data, additional sensor data 64, such as acceleration data 64a acquired with an acceleration sensor 32, position data 64b acquired with a position sensor 48 and medical data 64c acquired with a medical data sensor 34, may be received and processed by the situation classifier 61.

As shown in FIG. 2, the situation classifier 61 may comprise an additional data classifier 62 into which the additional sensor data 64, such as at least one of the acceleration data 64a, position data 64b and medical data 64c, is input. The additional data classifier 62 may be a program module run in the mobile device 14. From the additional sensor data 64, the additional data classifier 62 generates additional data classification values 66, which may encode properties of the additional data 64, such as head movement, a position of the user (at home, in office, etc.), stress of the user (which may be determined from the medical data 64c), etc.

It also may be that user input 65, which is input into the hearing system 10 by the user, for example via the knob 28 and/or the user interface 50, is further input data of the situation classifier 61. The user input 65 may be input into the additional data classifier 62, which also may classify its input data based on the user input 65. For example, it may be evaluated, how often a user has selected a specific program or that modifiers have been adjusted manually.

The user input 65 may also provide ground truth or suggest labels for the data 56, 64. The user may attribute, confirm, and/or enter data labels as well as properties of the specific situation of interest via the knob 28 and/or the user interface 50.

The sound classification values 60 and the additional data classification values 66 are input into a situation identifier 68, which may be seen as a further subcomponent of the situation classifier 61. For example, the situation identifier 68 may be implemented as program module in the hearing device 12 or the mobile device 14.

The situation identifier 68 may classify the sound classification values 60 and the additional data classification values 66 into situations 72, in particular into situation 72 of interest and situation 72 of disinterest. This classification may be performed by comparing the classification values 60, 66 with threshold values for detecting the situation 72. However, also more complicated ways of classifying the situation 72, for example, via parameterizable decision trees, are possible.

The situation identifier 68 or more general the situation classifier 61 comprise configuration parameters 70, which are used for defining and/or encoding situation 72 and/or whether these situations 72 are of interest or disinterest. For example, the configuration parameters 70 may comprise the above-mentioned thresholds.

The configuration parameters 70 may be changed and/or adapted during the operation of the hearing system 10 in the field. The configuration parameters 70 for the classifier 61 for a specific situation 72 of interest or disinterest may be sent from the storage system 54 to a plurality of hearing systems 10. In such a way, situations 72 of interest or disinterest may be defined at the site of the storage system 54, for example by a hearing aid manufacture, which then may collect interesting sensor data, as will be described below.

In summary, with the situation classifier 61, a situation 72 of interest or disinterest may be detected by classifying at least a part of the sensor data 56, 64. It has to be noted that not all sensor data 56, 64 generated may be used for classification. It may be that solely the sound data 56 is classified into situations 72 and that the additional data 64 is also collected (see below).

The situation classifier 61 may be designed differently as described with respect to FIG. 2, for example, may be implemented solely in the hearing device 12 or the mobile device 14 and/or may have more or less subcomponents.

The detected situation 72, which may be a simple yes/no-value (situation of interest yes/no), is input into a sensor data collector 74. The sensor data collector 74 may collect the sensor data 56, 64, when the hearing system 10 is in a situation 72 of interest and may discard the sensor data 56, 64, when the hearing system 10 is in a situation 72 of disinterest. Collecting in this context may mean that the sensor data 56, 64 is buffered in a memory, such as 30, 42. Discarding may mean that the sensor data 56, 64 is not buffered.

The classifier 61 also may be adapted for labelling the sensor data 56, 64. For example, it may be that first sensor data from a first sensor 20 is collected, such as audio data 56 from the microphone 20 of the hearing device 12. The classifier 61 may generate a classification of second sensor data 56 from a second sensor 44, such as audio data 56 from the microphone of the mobile device 14. The first sensor data may then be labelled with the classification of the second sensor 44. The labelling may be collected together with the sensor data 56, 64. In selected time windows, for example when the hearing system 10 is in a mode of reduced operation, for example during night, the collected sensor data 76 is sent to the storage system 54. There, the collected and optionally labelled sensor data 76 is stored in a memory 80 of the storage system 54, where it may be further used for fitting, configuring and/or training of hearing devices 12.

It may be that the storage system 54 comprises a storage system classifier 78 for classifying, whether the collected sensor data 76 is sensor data of interest and that the storage system 54 solely stores collected sensor data of interest. The storage system classifier 78 may classify the collected sensor data 76 in different ways as the hearing system 10 and/or with more computational demanding classification algorithms. It also may be that automatic labelling of collected sensor data 76 is performed by the storage system classifier 78.

While the present technology has been illustrated and described in detail in the drawings and foregoing description, such illustration and description are to be considered illustrative or exemplary and not restrictive; the present technology is not limited to the disclosed embodiments. Other variations to the disclosed embodiments can be understood and effected by those skilled in the art and practising the claimed present technology, from a study of the drawings, the disclosure, and the appended claims. In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SYMBOLS 10 hearing system
12 hearing device
14 mobile device
15 part behind the ear
16 part in the ear
18 tube
20 microphone
22 sound processor
24 sound output device
26 processor
28 knob
30 memory
32 acceleration sensor
34 medical sensor
36 sender/receiver
38 sender/receiver
40 processor
42 memory
44 microphone
46 loudspeaker
48 position sensor
50 user interface
52 Internet
54 storage system
56 audio data
57 hearing programs
58 output audio signal
59 sound classifier
60 sound classification values
61 situation classifier
62 sensor data classifier
64 additional sensor data
64a acceleration data
64b position data
64c medical data
65 user input
66 sensor data classification values
68 situation identifier
70 configuration parameters
72 situation
74 sensor data collector
76 collected sensor data
78 storage system classifier
80 memory

The invention claimed is:

1. A method for collecting and storing sensor data of a hearing system, the method comprising:
  receiving the sensor data of a sensor of a hearing device of the hearing system, wherein the hearing device is worn by a user;
  detecting a situation of interest by classifying at least a part of the sensor data with a classifier implemented in the hearing system;
  collecting the sensor data, when the hearing system is in a situation of interest; and
  sending the collected sensor data to a storage system in data communication with the hearing system,
  wherein:
    the sensor data comprises at least one of motion data acquired with a motion sensor, position data acquired with a position sensor, or medical data acquired with a medical data sensor; and
    the classifier comprises an additional data classifier into which at least one of the motion data, position data, or the medical data are input.

2. The method of claim 1, wherein the classifier further comprises a sound classifier for classifying audio data, which is received by the hearing device and which is output by the hearing device to the user; and
  wherein classification values of the sound classifier are used for selecting hearing programs of the hearing device.

3. The method of claim 1,
  wherein user input into the hearing system is input into the classifier.

4. The method of claim 1,
  wherein classification values generated by the classifier are compared with threshold values for detecting a situation of interest.

5. The method of claim 1, further comprising:
  detecting a situation of disinterest by classifying at least a part of the sensor data with the classifier;
  wherein the sensor data is discarded, when the hearing system is in a situation of disinterest.

6. The method of claim 5,
  wherein the sensor data is collected, when the hearing system is not in a situation of disinterest.

7. The method of claim 1, further comprising:
  sending configuration parameters for the classifier for a specific situation of interest from the storage system to a plurality of hearing systems.

8. The method of claim 1,
  wherein first sensor data from a first sensor is collected;
  wherein the classifier generates a classification of second sensor data from a second sensor;
  wherein the first sensor data is labelled with the classification of the second sensor.

9. The method of claim 1,
  wherein the storage system comprises a further classifier for classifying whether the collected sensor data is sensor data of interest; and
  wherein the storage system solely stores collected sensor data of interest.

10. A method for collecting and storing sensor data of a hearing system, the method comprising:
  receiving the sensor data of a sensor of a hearing device of the hearing system, wherein the hearing device is worn by a user;
  detecting a situation of interest by classifying at least a part of the sensor data with a classifier implemented in the hearing system;
  collecting the sensor data, when the hearing system is in a situation of interest; and
  sending the collected sensor data to a storage system in data communication with the hearing system,
  wherein the hearing system comprises a mobile device carried by the user;
  wherein the mobile device is in wireless data communication with the hearing device;
  wherein at least a part of the classifier is implemented in the mobile device.

11. A method for collecting and storing sensor data of a hearing system, the method comprising:
  receiving the sensor data of a sensor of a hearing device of the hearing system, wherein the hearing device is worn by a user;
  detecting a situation of interest by classifying at least a part of the sensor data with a classifier implemented in the hearing system;
  collecting the sensor data, when the hearing system is in a situation of interest; and
  sending the collected sensor data to a storage system in data communication with the hearing system,
  wherein the storage system is connected via the Internet with the hearing system;
  wherein the collected sensor data is transmitted to the storage system in selected time windows.

12. A non-transitory computer-readable medium storing instructions, which when executed by a processor cause a device to perform a method, the method comprising:
  receiving sensor data of a sensor of a hearing device of a hearing system, wherein the hearing device is worn by a user;
  detecting a situation of interest by classifying at least a part of the sensor data with a classifier implemented in the hearing system;
  collecting the sensor data, when the hearing system is in a situation of interest; and
  sending the collected sensor data to a storage system in data communication with the hearing system,
  wherein:
    the sensor data comprises at least one of motion data acquired with a motion sensor, position data acquired with a position sensor, or medical data acquired with a medical data sensor; and
    the classifier comprises an additional data classifier into which at least one of the motion data, position data, or the medical data are input.

13. The non-transitory computer-readable medium of claim 12, wherein the classifier further comprises a sound classifier for classifying audio data, which is received by the hearing device and which is output by the hearing device to the user; and
  wherein classification values of the sound classifier are used for selecting hearing programs of the hearing device.

14. The non-transitory computer-readable medium of claim 12, wherein user input into the hearing system is input into the classifier.

15. The non-transitory computer-readable medium of claim 12, wherein classification values generated by the classifier are compared with threshold values for detecting a situation of interest.

16. The non-transitory computer-readable medium of claim 12, the method further comprising:
  detecting a situation of disinterest by classifying at least a part of the sensor data with the classifier, wherein the sensor data is discarded, when the hearing system is in a situation of disinterest.

* * * * *